(12) United States Patent
Bobadilla Fazzini et al.

(10) Patent No.: US 8,728,785 B2
(45) Date of Patent: May 20, 2014

(54) ADDITIVE FOR BIOLEACHING THAT IS SUBSTANTIALLY MADE UP OF THE LICANANTASE LIPOPROTEIN, AND BIOLEACHING PROCESS TO WHICH THIS ADDITIVE IS ADDED TO INCREASE THE RECOVERY OF COPPER

(75) Inventors: Roberto Bobadilla Fazzini, Santiago (CL); Pilar Angélica Parada Valdecantos, Santiago (CL); Ricardo Badilla Ohlbaum, Santiago (CL)

(73) Assignee: Biosigma S.A., Colina, Santiago (CL)

( * ) Notice: Subject to any disclaimer, the term of this patent is extended or adjusted under 35 U.S.C. 154(b) by 0 days.

(21) Appl. No.: 13/390,488

(22) PCT Filed: Aug. 13, 2010

(86) PCT No.: PCT/IB2010/053673
§ 371 (c)(1),
(2), (4) Date: Feb. 14, 2012

(87) PCT Pub. No.: WO2011/024096
PCT Pub. Date: Mar. 3, 2011

(65) Prior Publication Data
US 2012/0208257 A1  Aug. 16, 2012

(30) Foreign Application Priority Data
Aug. 24, 2009 (CL) .................................. 1767-2009

(51) Int. Cl.
*C12N 9/00* (2006.01)
*C02F 3/34* (2006.01)
*C07H 21/04* (2006.01)
*C21B 15/00* (2006.01)
*B01D 11/00* (2006.01)

(52) U.S. Cl.
USPC ............... 435/183; 435/262; 75/743; 75/638; 423/27; 536/23.2

(58) Field of Classification Search
None
See application file for complete search history.

(56) References Cited

U.S. PATENT DOCUMENTS 4,497,778 A   2/1985   Pooley
2009/0126532 A1   5/2009   Kohr et al.

OTHER PUBLICATIONS

International Search Report for International Application No. PCT/IB2010/053673 Jan. 24, 2011.
UNIPROT Accession No. B5EP90—Apr. 14, 2009. Retrieved from the Internet on Jan. 6, 2010—http://www.uniprot.org/uniprot/B5EP90.txt?version=5.

*Primary Examiner* — Iqbal H Chowdhury
(74) *Attorney, Agent, or Firm* — Merchant & Gould P.C.

(57) ABSTRACT

The invention discloses an additive for bioleaching that makes it possible to increase the recovery of copper from sulfide ores. In which this additive is substantially made up of the Licanantase lipoprotein and a solution of sulfuric acid with a pH of 0.8 to 3. The Licanantase lipoprotein that has an amino acid sequence with at least 50% homology regarding the sequence defined in SEQ ID No. 1 or is the product of translation of a nucleotide sequence with at least 50% homology regarding the sequence defined in SEQ ID No. 2. It also protects the improved bioleaching process that includes adding the additive during the ore bioleaching process as defined in the present invention; and continuing with the habitual process, obtaining copper recoveries increased 5 to 20%.

5 Claims, 4 Drawing Sheets

SEQUENCE LISTING

```
<160> NUMBER OF SEQ ID NOS: 5

<210> SEQ ID NO 1
<211> LENGTH: 101
<212> TYPE: PRT
<213> ORGANISM: Artificial Sequence
<220> FEATURE:
<223> OTHER INFORMATION: Acidithiobacillus ferrooxidans and
      Acidithiobacillus thiooxidans

<400> SEQUENCE: 1

Met Ser Lys Phe Thr Thr Ala Leu Lys Val Thr Ala Leu Ile Leu Pro
1               5                   10                  15

Leu Gly Leu Ala Gly Cys Ala Thr Ser Ser Asp Leu Ala Lys Val Ser
            20                  25                  30

Ala Lys Ala Asp Ala Ala Gln Ser Thr Ala Asn Glu Ala Leu Ala Lys
        35                  40                  45
```

Ala Asn Ala Ala Gln Ser Thr Ala Thr Asp Ala Leu Ser Lys Ala Asn
         50                  55                  60

Ala Ala Gln Ser Thr Ala Asp Gln Ala Met Ser Thr Ala Asn Ser Ala
 65                  70                  75                  80

Asn Gln Lys Ala Glu Glu Ala Asn Glu Lys Val Glu Arg Met Phe Lys
                 85                  90                  95

Lys Ala Met Met Lys
            100

<210> SEQ ID NO 2
<211> LENGTH: 306
<212> TYPE: DNA
<213> ORGANISM: Artificial Sequence
<220> FEATURE:
<223> OTHER INFORMATION: Acidithiobacillus ferrooxidans and
      Acidithiobacillus thiooxidans

<400> SEQUENCE: 2
atgagcaagt ttaccacagc tttgaaagta actgcgctga ttttgcccct gggcctggcc     60
ggttgcgcta ccagttctga cctcgctaag gtttctgcca aggctgatgc cgcgcagtcc    120
accgccaacg aggctcttgc caaggccaat gccgcacaga gcactgcaac tgacgctttg    180
agcaaggcta atgccgcaca gagcacggct gatcaggcca tgagcactgc caattctgcc    240
aaccagaagg ctgaagaagc caatgagaag gtagagcgca tgttcaaaaa ggcgatgatg    300
aagtaa                                                              306

<210> SEQ ID NO 3
<211> LENGTH: 14
<212> TYPE: PRT
<213> ORGANISM: Artificial Sequence
<220> FEATURE:
<223> OTHER INFORMATION: Acidithiobacillus ferrooxidans and
      Acidithiobacillus thiooxidans

<400> SEQUENCE: 3

Ala Asp Ala Ala Gln Ser Thr Ala Asn Glu Ala Leu Ala Lys
 1               5                  10

<210> SEQ ID NO 4
<211> LENGTH: 24
<212> TYPE: PRT
<213> ORGANISM: Artificial Sequence
<220> FEATURE:
<223> OTHER INFORMATION: Acidithiobacillus ferrooxidans and
      Acidithiobacillus thiooxidans

<400> SEQUENCE: 4

Ala Asn Ala Ala Gln Ser Thr Ala Thr Asp Ala Leu Ser Lys Ala Asn
 1               5                  10                  15

Ala Ala Gln Ser Thr Ala Asp Gln
                 20

<210> SEQ ID NO 5
<211> LENGTH: 10
<212> TYPE: PRT
<213> ORGANISM: Artificial Sequence
<220> FEATURE:
<223> OTHER INFORMATION: Acidithiobacillus ferrooxidans and
      Acidithiobacillus thiooxidans

<400> SEQUENCE: 5

Ala Glu Glu Ala Asn Glu Lys Val Glu Arg
 1               5                  10

ADDITIVE FOR BIOLEACHING THAT IS SUBSTANTIALLY MADE UP OF THE LICANANTASE LIPOPROTEIN, AND BIOLEACHING PROCESS TO WHICH THIS ADDITIVE IS ADDED TO INCREASE THE RECOVERY OF COPPER

This application is a National Stage Application of PCT/IB2010/053673, filed 13 Aug. 2010, which claims benefit of Serial No. 1767-2009, filed 24 Aug. 2009 in Chile and which applications are incorporated herein by reference. To the extent appropriate, a claim of priority is made to each of the above disclosed applications.

OBJECTIVE OF THE INVENTION

The invention discloses a bioleaching additive that makes it possible to increase the recovery of copper in a bioleaching system. In which this additive is substantially made up of Licanantase lipoprotein and a solution of sulfuric acid at a pH of 0.8 to 3. The Licanantase lipoprotein has an amino acid sequence with at least 50% homology regarding the sequence defined in SEQ ID No. 1 or is the product of translation of a nucleotide sequence with at least 50% homology regarding the sequence defined in SEQ ID No. 2.

It also protects the improved bioleaching process that includes providing a bioleaching system; adding an additive for bioleaching as defined in the present invention; and continuing with the habitual bioleaching process, achieving increased copper recovery.

STATE OF THE ART

Copper sulfide ore processing is at present sustained by technologies based on physical and chemical processes associated with crushing, grinding and flotation of the ores, followed by fusion-conversion of the concentrates and electrolytic refining of the metal. In practice, over 80% of copper is produced by processing ores following the previously described route—known as conventional—that is limited to high and medium grade ores, depending on the specific characteristics of the ore deposits and processing plants. Because of this, there are vast and valuable relatively low-grade mineral resources that with conventional techniques are sub-economic, and remain unexploited for lack of an effective technology to work them with.

It has been established for a long time that sulfide ore solubilization or leaching is aided by the presence of iron and sulfur-oxidizing bacteria, a process known as bioleaching (Rawlings D E; *Biomineralization of metal-containing ores and concentrates, TRENDS in Biotechnology*, Vol. 21 No. 1, p38-42, 2003).

Bioleaching is defined as a method for solubilizing metals from complex matrixes in an acid environment, employing the direct or indirect action of microorganisms. The microorganisms that are useful in these processes belong both to the domain Bacteria and to the domain Archaea, and comply with two basic conditions, they are acidophilic and chemolithotrophic. Within the biomining microbiological community there are bacteria of the *Acidiphilium* spp., *Leptospirillum* spp., *Sulfobacillus* spp. genre and of the *Acidithiobacillus ferrooxidans* and *Acidithiobacillus thiooxidans* species; and archaea of the *Acidianus* spp., *Ferroplasma* spp., *Metallosphaera* spp., *Sulfolobus* spp. and *Thermoplasma* spp. genre. The most important microorganisms of this list are undoubtedly the *Acidithiobacillus ferrooxidans* and *Acidithiobacillus thiooxidans* bacteria.

It has been proposed that the participation of microorganisms in the bioleaching process can be direct and/or indirect (Rawlings D E. *Characteristics and adaptability of iron-and sulphur-oxidizing microorganisms used for the recovery of metals from minerals and their concentrates*. Microb Cell Fact. 2005 May 6; 4(1):13). For example, *Acidithiobacillus ferrooxidans* and *Acidithiobacillus thiooxidans* are capable of catalyzing the oxidization of reduced-sulfur-compounds (such as sulfide, elemental sulfur, thionates, etc.) employing oxygen as an electron acceptor and generating sulfuric acid as a final product, and reducing species such as sulfite and thiosulfate, as intermediate products, a process that makes it possible to directly or indirectly solubilize the metals associated with sulfides in the ore, lowering the formation of passivating substances on the reactive surface of the ore allowing the action of oxidizing elements, or directly by transferring electrons from the ore to the biomass formation. *Acidithiobacillus ferrooxidans* is capable of catalyzing the oxidization of iron (II) to iron (III) using the oxygen as an electron acceptor; the iron (III) that is generated is a great oxidizing agent that can oxidize the sulfides that are present or any compound that needs to be oxidized.

The traditional mining practice in bioleaching processes is to keep the ore in an acid medium, usually sulfuric acid, and to remove this acid medium to recover the metal through solvent extraction and electrowinning. The most used bioleaching systems are, in descending order, columns, gabions, heaps, dumps and stirred tanks.

Several processes oriented to improving or accelerating the bioleaching process of the traditional method, have been published. One approach, used for example in U.S. Pat. No. 6,110,253 (Kohr et al., 2000), is to increase the temperature of the bioleaching heaps to at least 50° C. Another example is the publication WO 2005/073414 (Du Plessis and De Kock, 2005), which proposes alternatively to increase the heap temperature, or increase the carbon content of the heap, by adding carbon dioxide, carbonate ores, or organic carbon compounds.

Another approach has been to incorporate selected biomass, such as, for example, strains with an increased oxidizing capability as is the case of the Wenelen *Acidithiobacillus ferrooxidans* DSM 16786 (Patent CL 44.546 and U.S. application Ser. No. 11/256,221) or Licanantay *Acidithiobacillus thiooxidans* DSM 17318 (application CL 2101-2005 and U.S. application Ser. No. 11/506,031), both property of BioSigma S.A., into a bioleaching system.

The present invention approaches the technical problem of optimizing the recovery of copper from ore in any bioleaching system, and achieves it by means of an additive that—added to any bioleaching system—improves the copper-recovery efficiency of this bioleaching process. Therefore, the invention is complementary to all the other existing strategies for increasing the efficiency of a bioleaching system.

The additive of the present invention, as mentioned above, substantially consist of the addition of the lipoprotein Licanantase in a solution of sulfuric acid at a pH of 0.8 to 3 to a bioleaching process. There are no similar additives in the state of the art, neither function nor composition wise. The Licanantase lipoprotein was first found in the supernatants of cultures of pure *Acidithiobacillus thiooxidans*, or combined with *Acidithiobacillus ferrooxidans*, in bioreactors of BioSigma S.A.; the inventors isolated and sequenced it, and established its use in the additive of the invention.

This protein had not been described in the state of the art, in fact, the closest publication, by Zhang et al. (Trans Nonferrous Met. Soc. China 18 (2008)1398-1402) describes lipoproteins of *A. ferrooxidans*, associated with external cell structures, because they are isolated after treating the cell pellet with hot acid water. This publication does not allot a function to the lipoproteins found, nor is their sequence described; it only classifies by peptide mass studies (peptide mass fingerprints) and computer analyses of the possible functionalities of the peptides found. On the contrary, the present invention surprisingly established that one protein in particular, Licanantase, can be used in an additive that increases copper recovery in a bioleaching system.

DESCRIPTION OF THE INVENTION

The invention discloses an additive for bioleaching that makes it possible to increase copper recovery in a bioleaching system. In which this additive is substantially made up of Licanantase and a solution of sulfuric acid at a pH of 0.8 to 3 in the bioleaching conditions, in which the Licanantase lipoprotein has an amino acid sequence with at least 50% homology regarding the sequence defined in SEQ ID No. 1 or is the product of translation of a nucleotide sequence with at least 50% homology regarding the sequence defined in SEQ ID No. 2.

The additive of the invention specifically contains 5 to 99% of the Licanantase lipoprotein; and 1 to 95% of a solution of sulfuric acid at a pH of 0.8 to 3. This protein can be produced by enriching it from total extracts, from extracts of secretomes, by cloning, or by any other technique available in the state of the art for the production of proteins.

A second aspect of the invention focuses on the improved bioleaching process that includes: providing a bioleaching system; adding the additive for the bioleaching as defined in the present invention; and continuing with the habitual bioleaching process increasing the recovery of copper in bioleaching systems by 5 to 20%.

The Licanantase lipoprotein, an active agent of the additive of the present invention, is found in the secreted protein fraction or secretome of *Acidithiobacilli bacteria*, especially of *Acidithiobacillus ferrooxidans* and *Acidithiobacillus thiooxidans* species.

The bioleaching process involves the interaction of bacteria with the ore in an interface, which is mainly composed of an exopolysaccharide extracellular matrix, in which cell products such as proteins and metabolites play an important role. On the other hand, the proteins located in the external membrane and the periplasm, such as transport proteins, and enzymes, are key elements in sulfide and iron oxidizing, allowing copper to be released from the ore. The fundamental interactions occur in the bacteria-mineral interface, including bacterial adherence processes and exchange of electrons that possibly induces the bioleaching process. The inventors have discovered that bioleaching strains, in pure and mixed cultures, secrete a particular group of proteins that would potentially play key roles in making the bioleaching of sulfide ores possible.

Based on the above, the inventors characterized the proteins secreted into the extracellular space in pure cultures of *Acidithiobacillus ferrooxidans, Acidithiobacillus thiooxidans* (secretome) and in mixed cultures of these 2 bacteria (metasecretome), grown in elemental sulfur as sole source of energy. This is for identifying the proteins that could be capable of interacting with insoluble substrates, and contributing to understanding the bacteria-mineral interactions that command bioleaching processes.

It was found that the total quantity of secreted protein in these cultures in the late exponential phase (approx. $1.00E+09$ cells/mL) are within the range of 0.5 to 2 mg/L, and only in cultures that include *A. thiooxidans*. Considerable amounts of protein secreted in pure *A. ferrooxidans* cultures were not found, though the proteins of the metasecretome are different to those of the secretome of pure *A. thiooxidans*, indicating that *A. ferrooxidans* secretes proteins as it interacts with *A. thiooxidans* or that it alters the *A. thiooxidans* secretion pattern.

The concentration of secreted protein, of 0.5 to 2 mg/L, is relatively low regarding what is observed in other species, for example, protein secretion close to 200 mg/L has been informed for *Bacillus* sp.

Firstly, with the purpose of establishing their use as additives for bioleaching, the secretomes obtained were concentrated five times, and assays were conducted with these concentrates to observe their effect on bioleaching.

One of the characteristics of *Acidithiobacillus ferrooxidans* and *Acidithiobacillus thiooxidans* bacteria is that they are acidophilic and normally develop in media with a pH of 1 to 3, or even lower. In fact, culture media for these bacteria have a pH of 1.6. Therefore we can expect both the secretome of these bacteria, and the proteins that compose it, such as the Licanantase, to be stable within this same pH range. Therefore, all the tests carried out and the compositions obtained were kept to this pH, specifically within the range of pH 0.8 to pH 3. Sulfuric acid was used to acidify the compositions because is a diprotonated acid, it is itself a buffer that keeps the pH within the desired range (pKa 1.92).

Surprisingly it was observed that when added to a bioleaching system inoculated with *A. ferrooxidans* and *A. thiooxidans*, both the secretome of *A. thiooxidans* and the metasecretome of *A. ferrooxidans* and *A. thiooxidans* significantly increased the copper-recovery percentage by 6 to 8%, in an ore that is refractory to bioleaching, such as chalcopyrite; whereas there were no significant changes in the final biomass of the heaps compared with the control. This information has great economic importance to improve copper recovery in industrial bioleaching processes because it indicates that the processes involved in bioleaching are being specifically and directly affected and not, as had been done till now, improving bioleaching while increasing the biomass present.

Secondly, assays with fractions of the secretome were carried out in order to establish whether the effect observed corresponded to the activity of all the proteins of the secretome, or only to some or one of them. The fraction between 3.5 and 30 kDa, and the fraction larger than 30 kDa were tested. It was found that the fraction between 3.5 and 30 kDa showed an increase in the recovery of copper from the heap, whereas the larger fraction didn't show any effect.

Once the fraction that possessed the activity was identified, the inventors studied the proteins present in it, discovering that the lipoprotein present in largest amount in the fraction, the Licanantase lipoprotein, is responsible for the increase in copper recovery when added to bioleaching heaps.

This lipoprotein Licanantase was isolated from the supernatants of the BioSigma S.A. bioreactors, studied and sequenced, and its amino acid sequence is shown in SEQ ID No. 1. The inventors also specified the nucleotide sequence that codifies it, which is described in SEQ ID No. 2.

The SEQ ID No. 1 and SEQ ID No. 2 sequences obtained were compared to the sequences available in protein and gene databases of the National Center for Biotechnology Information (NCBI, EEUU) and of The Universal Protein Resource Knowledgebase (UniProtKB), using the public bioinformatics tool BLAST (Basic Local Alignment Search Tool). In the case of the amino acid sequence SEQ ID No. 1 it was found that at the time, there were only two close sequences published in NCBInr data bases with code ref|YP_002220838.1| (NCBInr) and UniProtKB with code B7J904_ACIF2; both correspond to the same amino acid sequence annotated as the putative lipoprotein of *Acidithiobacillus ferrooxidans* ATCC 53993 and the putative lipoprotein of *Acidithiobacillus ferrooxidans* ATCC 23270, respectively, with 96% homology to the amino acid sequence SEQ ID No. 1. These proteins correspond to the same putative protein identified based on the *A. ferrooxidans* ATCC 53993 (DOE Joint Genome Institute, EEUU) and *A. ferrooxidans* ATCC 23270 (Valdés et al., 2008 en BMC Genomics 9 (1), 597) sequencing projects, so they correspond to in silico annotations generated only from genomic information, with no experimental demonstration of the synthesis of this protein. The only result generated by the BLAST of nucleotide sequence Seq ID No. 2 against the data base of the NCBI was the genome sequence of both strains of *A. ferrooxidans* mentioned (ATCC 23270 code GenBank: CP001219.1 and ATCC 53993 code GenBank: CP001132.1) both with a 100% homology in the gene that would codify for the mentioned putative lipoprotein and with an 87% homology with SEQ ID No. 2, indicating that only one gene with a similar sequence has been published.

As it has been mentioned, this invention also aims at an improved bioleaching process which includes the following stages:
a) providing a bioleaching system;
b) adding the bioleaching additive made up of 10 to 99% of the Licanantase lipoprotein in acid, which has an amino acid sequence with at least 50% homology regarding the sequence defined in SEQ ID No. 1 or is codified by a nucleotide sequence with at least 50% homology regarding the sequence defined in SEQ ID No. 2 and
c) continuing with the habitual bioleaching process.

The bioleaching system can be any known bioleaching system, such as columns, gabions, heaps, dumps or stirred tanks. The additive is added with a concentration of 0.01 to 100 mg/L with which the process is able to obtain copper recovery increased 5 to 20% regarding processes without stage b).

Although the Licanantase lipoprotein is responsible for the effect, our results show that its action does not diminish in the presence of the other proteins present in the secretome, so it can be used as an additive for bioleaching the Licanantase lipoprotein, the fraction between 3.5 and 30 KDa, or all the secreted protein fraction, obtaining the same increase results in copper recovery.

As we have shown, the Licanantase lipoprotein has an amino acid sequence with at least 50% homology regarding the sequence defined in SEQ ID No. 1 or is the translation product of a nucleotide sequence with at least 50% homology regarding the sequence defined in SEQ ID No. 2. In less preferred options of the invention, it is defined that the Licanantase lipoprotein has an amino acid sequence with homology regarding the sequence defined in SEQ ID No. 1 of at least 60%, or 70% or 80%; or it is defined that the Licanantase lipoprotein is codified by a nucleotide sequence with homology regarding the sequence defined in SEQ ID No. 2 of at least 60%, or 70% or 80%.

DESCRIPTION OF THE FIGURES

FIG. 3 A. 1 shows the increase in the recovery of copper in solution when the complete secretome of *A. thiooxidans* is added.

FIG. 3 B. 1 shows the increase in the recovery of copper in solution when the complete secretome of the mixture of *A. thiooxidans+A. ferrooxidans* is added. You can observe that both the secetome of *A. thiooxidans* and that of the *A. thiooxidans+A. ferrooxidans* mixture show a significant increase in copper recovery. The presence of the Licanantase lipoprotein has been detected in both cases.

FIG. 3 C. 1 shows the recovery of copper in solution by bioleaching in the presence of the 3.5 to 30 KDa fraction of the secretome of *A. thiooxidans* enriched in Licanantase lipoprotein and of the larger fraction of 30 KDa of the secretome of *A. thiooxidans*.

We can be observe that only the 3.5 to 30 KDa fraction of the secretome of *A. thiooxidans* enriched in the Licanantase protein shows a significant increase in the recovery of copper.

Figure 3:
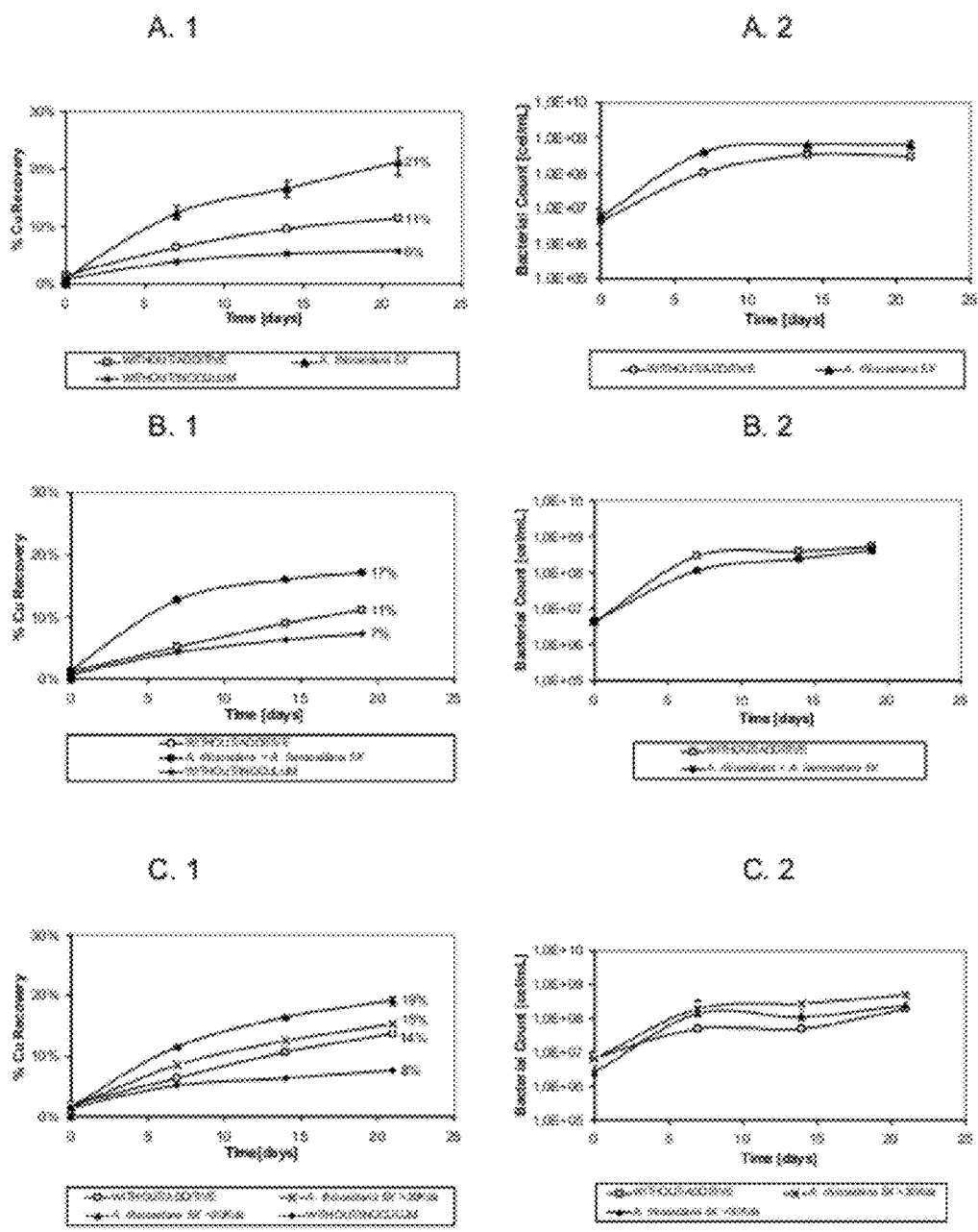
FIG. 3 shows 3 graphs illustrating the recovery of copper in the presence of different fractions of the secretome.

FIG. 3 A. 2 shows the variation in total biomass (*A. thiooxidans* and *A. ferrooxidans*) inoculated when the complete secretome of *A. thiooxidans* is added.

FIG. 3 B. 2 shows the variation in the total biomass (*A. thiooxidans* and *A. ferrooxidans*) inoculated when the complete secretome of the *A. thiooxidans+A. ferrooxidans* mixture is added.

FIG. 3 C. 2 shows the variation in the total biomass (*A. thiooxidans* and *A. ferrooxidans*) inoculated in the presence of the 3.5 to 30 KDa fraction of the *A. thiooxidans* secretome enriched in Licanantase lipoprotein, and of the fraction larger than 30 KDa of the *A. thiooxidans* secretome.

We can observe that neither addition of the total secretome nor of the 3.5 to 30 kDa fraction enriched in Licanantase lipoprotein affect the normal growth of total biomass in any of the bioleaching assays.

Figure 4:
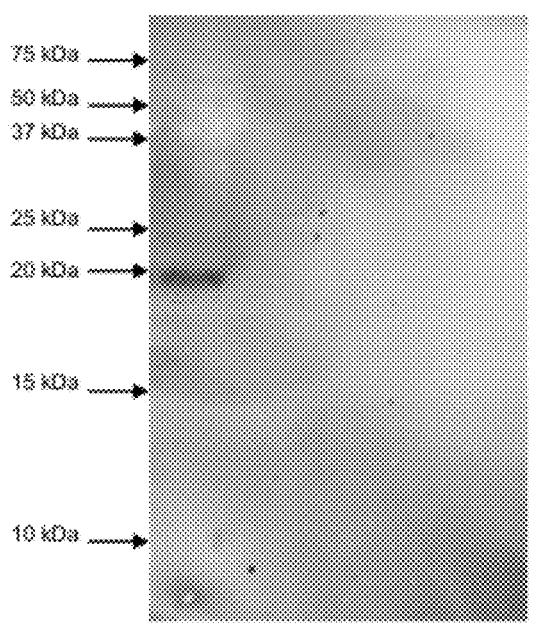

FIG. 4 shows an autoradiography based on a 15% denaturing polyacrylamide gel electrophoresis with the product of Licanantase cloning in *E. coli* BL21 with the protein marked for detection by chemiluminescence.

APPLICATION EXAMPLES

Example 1

Methodologies for Concentration and Analysis of Licanantase 1.1 Concentration of Licanantase for Bioleaching Assays

*Acidithiobacillus thiooxidans* cultures grown in a minimal medium (990 mg/L $(NH_4)_2SO_4$, 145 mg/L $NaH_2PO_4.H_2O$, 52 mg/L $KH_2PO_4$, 100 mg/L $MgSO_4.7H_2O$, 21 mg/L $CaCl_2$, pH 1.6) supplemented with elemental sulfur at 1% p/v, and cultivated with orbital shaking at 30° C. were collected, sonicated 1 min with 50% intensity in a sonication bath (Wise-Clean, Daihan) and centrifuged at 5,000×g for 15 minutes at 4° C.

1.1.1 Production of Concentrates 5× (5 Times) of Secretomes

The supernatant obtained was centrifuged again under the same condition and then filtered (0.2 μm). 100-10,000 mL of filtered culture was concentrated by evaporation under vacuum (40° C., 100 mBar) in RapidVap concentrator equipment (Labconco) till a reduction of 5 to 10 times the volume was achieved, and till a concentration of 5 to 10 mg of total protein/L was achieved. Extreme acidification of the medium was avoided by keeping the pH>1.0 by adding solution of NaOH 1 M.

The concentrate obtained was dialyzed against acid water (distilled water acidified with sulfuric acid at a 1.6 pH), by means of a 3.5 kDa membrane (SnakeSkin®, Thermo Fisher Scientific) at 4° C., overnight.

1.1.2 Production of Different Fractions of Secretomes

In order to test a Licanantase-enriched fraction, the dialyzate was filtered in ultrafiltration membranes with pore size 30 kDa (Amicon® Ultra-15, Millipore) obtaining a filtrate containing the 3.5 to 30 kDa Licanantase-enriched fraction and the >30 kDa fraction, in a medium acidified with sulfuric acid at pH 1.6.

1.2 Licanantase Analysis and Identification

The filtrate obtained in point 1.1, above, was precipitated using a commercial protein-precipitation kit (2D-Cleanup kit, GE Healthcare) following the manufacturer's instructions. The precipitate was completely resuspended in a solution composed of Urea 7 M, Tiourea 2 M, CHAPS 4% w/v and Trizma base 20 mM, and the concentration of proteins was quantified by spectrophotometry at 595 nm using the Bradford method.

Figure 1:
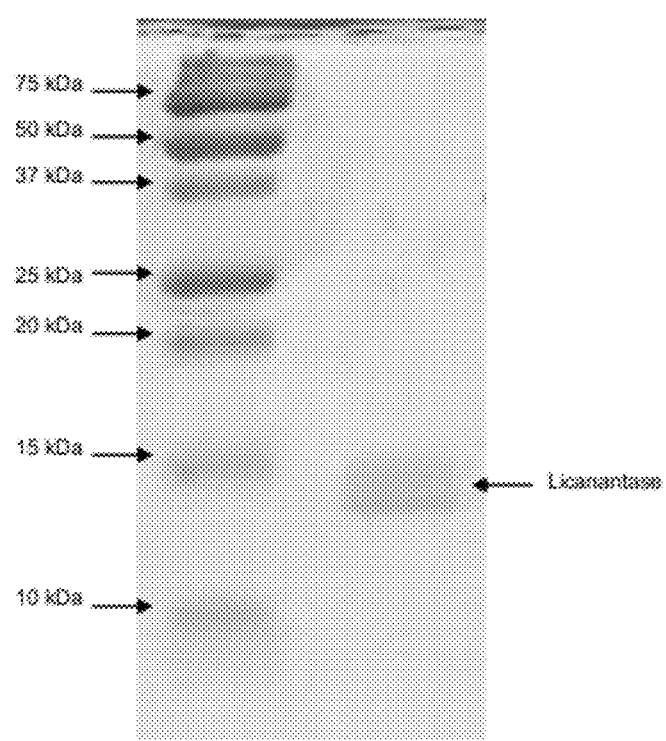
FIG. 1 shows a 15% denaturing polyacrylamide gel electrophoresis in which the Licanantase lipoprotein was obtained by concentrating the secretome of *A. thiooxidans* cultures grown in 1% sulfur for bioleaching assays.

Between 5 to 20 µg of total protein were analyzed by electrophoresis in 15% polyacrylamide gels under denaturing conditions; a band was observed in the range of 10 to 15 kDa corresponding to Licanantase (FIG. 1).

The band was manually cut away from the gel and treated with a commercial protein-digestion kit (In-Gel tryptic digestion kit, Pierce). The peptides resulting from the digestion were analyzed by liquid chromatography coupled to Mass Spectrometry (LC/MS and MS/MS) using an Orbitrap XL Mass Spectrometer (Thermo Fisher Scientific).

The mass spectra generated were analyzed with Xcalibur software (Thermo Scientific), producing a list of peptide masses that were identified with SEQUEST and X!tandem search engines against the NCBInr public database, adding the genome sequences of $A.$ $ferrooxidans$ DSM 16786 and $A.$ $thiooxidans$ DSM 17318 strains, property of BioSigma S.A.

In this way, the peptides ADAAQSTANEALAK (SEQ ID NO: 3); ANAAQSTATDALSKANAAQSTADQ (SEQ ID NO: 4) and AEEANEKVER (SEQ ID NO: 5) were identified by ab initio sequencing, with an identification probability of 100% for the Licanantase protein.

Sequences SEQ ID No. 1 and SEQ ID No. 2 were obtained based on "shot-gun" sequencing and annotation of the $A.$ $thiooxidans$ DSM 17318 genome carried out by the company AgenCourt (EEUU).

2. Bioleaching Assays

Figure 2:
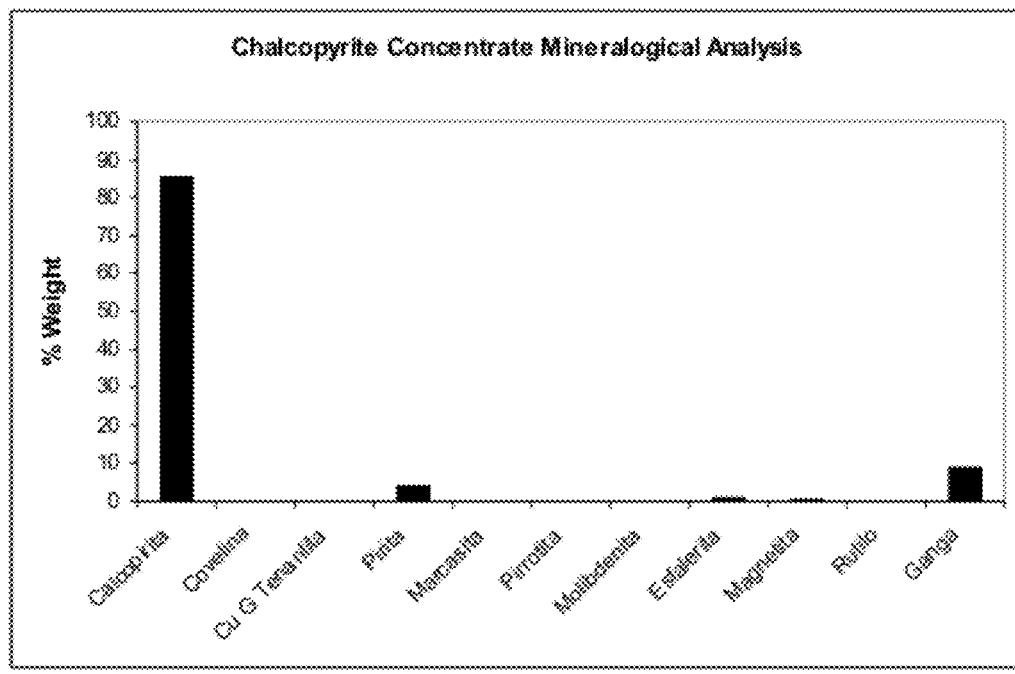
FIG. 2 shows the mineralogical analysis of the chalcopyrite concentrate used in the bioleaching assays, indicating that the chalcopyrite ore reaches 85.5% of the total composition, representing over 99% of the Cu present.

The bioleaching assays were carried out in flasks, always in duplicate. Each flask with 100 mL of minimal medium (pH 1.6) supplemented with essential salts: 990 mg/L $(NH_4)_2SO_4$, 145 mg/L $NaH_2PO_4.H_2O$, 52 mg/L $KH_2PO_4$, 100 mg/L $MgSO_4.7H_2O$, 21 mg/L $CaCl_2$, 1.5 g/L of Fe (III), 2.5 g/L of Fe (II) in the presence of 1% $^P/_v$ chalcopyrite Concentrate. The composition of this concentrate is shown in FIG. 2; chalcopyrite mineral is as much as 85.5% of the total composition, representing over 99% of the Cu (II) present.

Mineralogical analysis of the chalcopyrite Concentrate was carried out by optic reflection, preparing briquettes from representative samples split into 3-g pieces, trimmed and polished, using the point-counting statistical method.

The culture medium was inoculated with a mixture of $A.$ $thiooxidans$ and $A.$ $ferrooxidans$ in equal quantities (1.00E+007 cell/mL each).

Two controls were carried out in each case, in the first place culture medium on its own, without bacterial inoculum nor additive (WITHOUT/INOCULUM), which accounts for copper chemical leaching always present; and secondly, culture medium with bacterial inoculum without additive (WITHOUT/ADDITIVE), which explains standard bioleaching, to compare it with improved bioleaching in which the additive of this is invention is incorporated.

The flasks were incubated at 30° C., stirred for 21 days, and submitted to weekly count determinations for cells, total iron, iron (II) and copper (II) in the supernatant, using the following techniques:

2.0.1 Cell Counting

The concentration of $A.$ $thiooxidans$ and $A.$ $ferrooxidans$ cells in the bioleaching assays was monitored through cell counts in a Thoma Chamber (Thoma Chamber, 0,010 mm deep) with optical microscopy (Olympus microscope, model CX31).

2.0.2 Determination of Concentrations of Copper, and Iron Species in Solution Copper Cu(II), and total iron determinations were carried out through analysis with atomic absorption spectrometry (Perkin Elmer Aanalyst 400 model). Concentration of Fe(II) was carried out by determination with o-phfenanthroline.

2.1 Addition of the Complete Protein-Fraction of the Secretome

First of all, studies were made in which the complete protein fraction of the secretome of both $A.$ $thiooxidans$ (FIG. 3 A. 1) and the mixture of $A.$ $thiooxidans$ and $A.$ $ferrooxidans$ (FIG. 3 B. 1) concentrated 5 times and containing approximately 5 mg of total protein/L at pH 1.6 were added. It can be observed that both the secretome of $A.$ $thiooxidans$ and the metasecretome of the mixture of $A.$ $thiooxidans$ and $A.$ $ferrooxidans$ show a significant increase in the recovery of copper.

FIG. 3A 1 shows the percentage of copper recovery when the secretome of $A.$ $thiooxidans$ concentrated 5 times is added; we can observe that on day 21, copper recovery is 10% higher than with normal bioleaching without the additive. FIG. 3A 2 shows that the biomass remained similar in both assays so we can conclude that the secretome of $A.$ $thiooxidans$ 5× directly affects bioleaching processes.

FIG. 3B. 1 shows the percentage of copper recovery when the metasecretome of the mixture of $A.$ $thiooxidans$ and $A.$ $ferrooxidans$ concentrated 5 times, is added; we can observe that on day 21 copper recovery is 6% higher than with normal bioleaching without additive. We can observe in FIG. 3B. 2, that the biomass remained similar in both assays and we therefore can conclude that the metasecretome of the mixture of $A.$ $thiooxidans$ and $A.$ $ferrooxidans$ 5× directly affects bioleaching processes.

2.2 Addition of Different Fractions of the Secretome of $A.$ $Thiooxidans$

Assays were carried out adding the 3.5 to 30 KDa fraction of the secretome of $A.$ $thiooxidans$ enriched in the Licanantase protein and the larger 30 KDa fraction of the secretome of *A. thiooxidans* obtained according to the description in example 1.1.2; results are shown in FIG. 3C.1. We can observe that only the 3.5 to 30 KDa fraction of the secretome of *A. thiooxidans* shows a significant increase in copper recovery.

FIG. 3C.1 shows the percentage of copper recovery when the different fractions of the *A. thiooxidans* secretome, concentrated 5 times, are added; we can see that on day 21, copper recovery is 5% higher with the addition of a fraction lower than 30 kDa than with normal bioleaching without additive, whereas when the fraction larger than 30 kDa is added, no significant differences compared to the control without additive, are observed. We can observe in FIG. 3C.2 that the biomass remained similar in the 3 assays, from which we can conclude that the lower-than-30 kDa fraction of the *A. thiooxidans* secretome 5×, directly affects bioleaching processes.

3. Licanantase Cloning

Once it had been concluded that the Licananatase lipoprotein has the enhancing effect on bioleaching, sequencing of this protein was begun. The amino acid sequence is shown in SEQ ID No. 1.

With the protein, work began on seeking the codifying sequence in the genome of *A. thiooxidans*, specifically in the genome of Licanantay DSM 17318, property of BioSigma S.A. (applications CL 2101-2005 and U.S. Ser. No. 11/506,031), and the licanantase gene, shown in SEQ ID No. 2, was found.

This gene was cloned in the pBM4_pnit_histag vector developed by BioSigma S.A. (applications CL 2115-2007 and U.S. Ser. No. 12/174,374), and incorporated into the *E. coli* BL21 strain, as below:

3.1 Gene Amplification

The licanantase gene was amplified by PCR using specific primers designed for adding the restriction sites for 5'HindIII and 3' NotI, and a histidine tail to locate and/or purify the expressed product.

Amplification conditions were: initializing step at 94° C. for 1 minute; ten cycles of: denaturation at 94° C. for 45 s; annealing at 52° C. for 45 s; extension at 72° C. for 1.5 minutes; followed by 25 cycles of: denaturation at 90° C. for 45 s; annealing at 52° C. for 45 s; extension at 72° C. for 1.5 minutes. Final elongation was carried out at 72° C. for 10 minutes, and the product of the reaction was stored at 4° C. till its purification, which was carried out using a purification kit for PCR products (QIAquick, QIAGEN).

3.2 Gene Cloning

The pBM4_pnit_histag plasmid was digested with a mixture of restriction enzymes HindIII/NotI for 6 hrs. at 37° C., followed by heat inactivation at 65° C. for 10 minutes, followed by precipitation in pure ethanol and resuspension in denaturalized water. The DNA obtained from the amplification and digestion steps was quantified in NanoDrop equipment and ligated in a proportion of 1:20 at 20° C. for 3 hrs. Transformation of the BL21 strain of *Escherichia coli* was carried out by electroporation using the standardized method of BioSigma S.A.

3.3 Expression of Licanantase in *E. Coli*.

The transforming strains were selected by growth in media supplemented with kanamycin and verified by PCR studies to determine the presence of the licanantase gene. The positive clones were grown in Luria-Bertani (LB) liquid media or minimal medium (LeMaster D M & Richards F M; *Preparative-Scale Isolation of Isotopically Labeled Amino Acids*, Analytical Biochemistry, Vol. 122, No. 2, p238-247, 1982) supplemented with 0.2% $^P/_v$ glucose and supplemented with kanamycin, until late exponential phase. Cells were harvested by centrifugation (at 10.000 rpm for 10 minutes at 4° C.) and the supernatant was filtered with 0.2 μm nitrocellulose filters, and concentrated by evaporation. At the same time, the harvested cells were washed twice with PBS (pH 7.4) and resuspended in a protein-resuspension buffer, and a total protein extract was then obtained.

The supernatant and the protein extract were loaded in a 15% polyacrylamide gel and submitted to SDS-PAGE at 150 V for 1 hr. The gel was transferred to a nitrocellulose membrane at 400 mA for 1 hr in a Criterion™ Blotter (BioRad). After the transference, the membrane was blocked and incubated with the His-Prob-HRP reagent and later with the chemiluminescent substrate SuperSignal® West Pico® (Pierce), and exposed to an autoradigraphic film.

The results can be seen in FIG. 4 in which the band shows the expression of Licanantase in *E. coli*.

The invention claimed is:
1. An additive for bioleaching, comprising:
   a) 5 to 99% by weight of a Licanantase lipoprotein having the amino acid sequence of SEQ ID NO:1; and
   b) 1 to 95% of a solution of sulfuric acid at a pH between 0.8 and 3.
2. The additive for bioleaching according to claim 1, wherein the Licanantase lipoprotein is encoded by a nucleotide sequence having the nucleotide sequence of SEQ ID NO:2.
3. The additive for bioleaching according to claim 1, the Licanantase lipoprotein having an activity of increasing copper bioleaching of *Acidithiobacillus thiooxidans* or *Acidithiobacillus ferrooxidans*.
4. A bioleaching process, wherein the process comprises:
   a) providing a bioleaching system;
   b) adding the additive for bioleaching as defined in claim 1; and
   c) continuing with the habitual bioleaching process.
5. The bioleaching process according to claim 4, wherein the additive is added in a concentration of 0.01 to 100 mg/L.

* * * * *